(12) United States Patent
Ek

(10) Patent No.: US 7,713,305 B2
(45) Date of Patent: May 11, 2010

(54) ARTICULAR SURFACE IMPLANT

(75) Inventor: Steven W. Ek, Bolton, MA (US)

(73) Assignee: ArthroSurface, Inc., Franklin, MA (US)

( * ) Notice: Subject to any disclaimer, the term of this patent is extended or adjusted under 35 U.S.C. 154(b) by 450 days.

(21) Appl. No.: 11/359,891

(22) Filed: Feb. 22, 2006

(65) Prior Publication Data

US 2006/0229726 A1  Oct. 12, 2006

Related U.S. Application Data

(63) Continuation-in-part of application No. 10/373,463, filed on Feb. 24, 2003, which is a continuation-in-part of application No. 10/162,533, filed on Jun. 4, 2002, now Pat. No. 6,679,917, which is a continuation-in-part of application No. 10/024,077, filed on Dec. 17, 2001, now Pat. No. 6,610,067, which is a continuation-in-part of application No. 09/846,657, filed on May 1, 2001, now Pat. No. 6,520,964.

(60) Provisional application No. 60/201,049, filed on May 1, 2000, provisional application No. 60/654,989, filed on Feb. 22, 2005.

(51) Int. Cl.
*A61F 2/38* (2006.01)
(52) U.S. Cl. .................. 623/20.14; 623/20.16
(58) Field of Classification Search .............. 623/21.11, 623/21.18, 23.44, 23.46, 20.34, 20.36, 20.33, 623/20.17, 23.54, 23.5, 20.14, 20.18, 20.19, 623/20.2, 20.16
See application file for complete search history.

(56) References Cited

U.S. PATENT DOCUMENTS

| | | | |
|---|---|---|---|
| 992,819 A | 5/1911 | Springer | |
| 1,451,610 A | 4/1923 | Gestas | |
| 2,267,925 A | 12/1941 | Johnston | |
| 3,176,395 A | 4/1965 | Warner et al. | |
| 3,840,905 A | 10/1974 | Deane | |
| 4,016,651 A | 4/1977 | Kawahara et al. | |
| 4,034,418 A | 7/1977 | Jackson et al. | |

(Continued)

FOREIGN PATENT DOCUMENTS

AU  2001262308  12/2001

(Continued)

OTHER PUBLICATIONS

Notice of Allowance issued in corresponding U.S. Appl. No. 10/618,887, dated Sep. 13, 2007.

(Continued)

*Primary Examiner*—Pedro Philogene
(74) *Attorney, Agent, or Firm*—Grossman Tucker Perreault & Pfleger, PLLC

(57) ABSTRACT

An implant for replacing a portion of an articular surface including a load bearing surface and a bone contacting region. The load bearing surface had a contour defined by a first curve string which is based on a contour of the articular surface being replaced in a first plane. The load bearing surface of the implant is further defined by the contour of the articular surface being replaced in a second plane, in which the first and second planes are mutually intersection planes.

13 Claims, 12 Drawing Sheets

U.S. PATENT DOCUMENTS

| | | | |
|---|---|---|---|
| 4,044,464 A | 8/1977 | Schiess et al. |
| 4,158,894 A | 6/1979 | Worrell |
| 4,344,192 A | 8/1982 | Imbert |
| 4,433,687 A | 2/1984 | Burke et al. |
| 4,462,120 A | 7/1984 | Rambert et al. |
| 4,474,177 A | 10/1984 | Whiteside |
| 4,484,570 A | 11/1984 | Sutter et al. |
| 4,531,517 A | 7/1985 | Forte et al. |
| 4,535,768 A | 8/1985 | Hourahane et al. |
| 4,634,720 A | 1/1987 | Dorman et al. |
| 4,655,752 A | 4/1987 | Honkanen et al. |
| 4,661,536 A | 4/1987 | Dorman et al. |
| 4,662,371 A | 5/1987 | Whipple et al. |
| 4,664,669 A | 5/1987 | Ohyabu et al. |
| 4,673,407 A | 6/1987 | Martin |
| 4,693,986 A | 9/1987 | Vit et al. |
| 4,712,545 A | 12/1987 | Honkanen |
| 4,714,478 A | 12/1987 | Fischer |
| 4,719,908 A | 1/1988 | Averill et al. |
| 4,729,761 A | 3/1988 | White |
| 4,823,780 A | 4/1989 | Odensten et al. |
| 4,842,604 A | 6/1989 | Dorman et al. |
| 4,896,663 A | 1/1990 | Vandewalls |
| 4,911,153 A | 3/1990 | Border |
| 4,927,421 A | 5/1990 | Goble et al. |
| 4,938,778 A | 7/1990 | Ohyabu et al. |
| 4,940,467 A | 7/1990 | Tronzo |
| 4,976,037 A | 12/1990 | Hines |
| 4,979,957 A | 12/1990 | Hodorek |
| 4,989,110 A | 1/1991 | Zevin et al. |
| 4,990,163 A | 2/1991 | Ducheyne et al. |
| 4,997,434 A | 3/1991 | Seedhom et al. |
| 4,998,938 A | 3/1991 | Ghajar et al. |
| 5,007,930 A | 4/1991 | Dorman et al. |
| 5,019,104 A | 5/1991 | Whiteside et al. |
| 5,053,049 A | 10/1991 | Campbell |
| 5,100,405 A | 3/1992 | McLaren |
| 5,127,920 A | 7/1992 | MacArthur |
| 5,192,291 A | 3/1993 | Pannek, Jr. |
| 5,201,881 A | 4/1993 | Evans |
| 5,211,647 A | 5/1993 | Schmieding |
| 5,224,945 A | 7/1993 | Pannek, Jr. |
| 5,255,838 A | 10/1993 | Gladdish, Jr. et al. |
| 5,263,498 A | 11/1993 | Caspari et al. |
| 5,263,987 A | 11/1993 | Shah |
| 5,282,863 A | 2/1994 | Burton |
| 5,290,313 A | 3/1994 | Heldreth |
| 5,312,411 A | 5/1994 | Steele |
| 5,314,478 A | 5/1994 | Oka et al. |
| 5,314,482 A | 5/1994 | Goodfellow et al. |
| 5,336,224 A | 8/1994 | Selman |
| 5,354,300 A | 10/1994 | Goble et al. |
| 5,358,525 A | 10/1994 | Fox et al. |
| 5,360,446 A | 11/1994 | Kennedy |
| 5,374,270 A | 12/1994 | McGuire et al. |
| 5,383,937 A | 1/1995 | Mikhail |
| 5,387,218 A | 2/1995 | Meswania |
| 5,395,401 A | 3/1995 | Bahler |
| 5,409,494 A | 4/1995 | Morgan |
| 5,413,608 A | 5/1995 | Keller |
| 5,423,822 A | 6/1995 | Hershberger |
| 5,458,643 A | 10/1995 | Oka et al. |
| 5,480,443 A | 1/1996 | Elias |
| 5,486,178 A | 1/1996 | Hodge |
| 5,509,918 A | 4/1996 | Romano |
| 5,520,695 A | 5/1996 | Luckman |
| 5,522,900 A * | 6/1996 | Hollister ............... 128/898 |
| 5,534,031 A | 7/1996 | Matsuzaki et al. |
| 5,540,696 A | 7/1996 | Booth, Jr. et al. |
| 5,580,353 A | 12/1996 | Mendes et al. |
| 5,593,450 A | 1/1997 | Scott et al. |
| 5,595,193 A | 1/1997 | Walus et al. |
| 5,601,550 A | 2/1997 | Esser |
| 5,616,146 A | 4/1997 | Murray |
| 5,620,055 A | 4/1997 | Javerlhac |
| 5,624,463 A | 4/1997 | Stone et al. |
| 5,632,745 A | 5/1997 | Schwartz |
| 5,645,598 A | 7/1997 | Brosnahan, III |
| 5,681,311 A | 10/1997 | Foley et al. |
| 5,682,886 A | 11/1997 | Delp et al. |
| 5,683,400 A | 11/1997 | McGuire |
| 5,683,465 A | 11/1997 | Shinn et al. |
| 5,683,466 A | 11/1997 | Viatle |
| 5,700,264 A | 12/1997 | Zucherman et al. |
| 5,700,265 A | 12/1997 | Romano |
| 5,702,401 A | 12/1997 | Shaffer |
| 5,702,465 A * | 12/1997 | Burkinshaw ............... 623/20.2 |
| 5,702,467 A | 12/1997 | Gabriel et al. |
| 5,741,266 A | 4/1998 | Moran et al. |
| 5,769,855 A | 6/1998 | Bertin et al. |
| 5,769,899 A | 6/1998 | Schwartz et al. |
| 5,771,310 A | 6/1998 | Vannah |
| 5,776,137 A | 7/1998 | Katz |
| 5,782,835 A | 7/1998 | Hart et al. |
| 5,810,851 A | 9/1998 | Yoon |
| 5,817,095 A | 10/1998 | Smith |
| 5,824,105 A | 10/1998 | Ries et al. |
| RE36,020 E | 12/1998 | Moore et al. |
| 5,882,350 A | 3/1999 | Ralph et al. |
| 5,885,297 A | 3/1999 | Matsen, III |
| 5,885,298 A | 3/1999 | Herrington et al. |
| 5,888,210 A | 3/1999 | Draenert |
| 5,893,889 A | 4/1999 | Harrington |
| 5,895,390 A | 4/1999 | Moran et al. |
| 5,911,126 A | 6/1999 | Massen |
| 5,918,604 A | 7/1999 | Whelan |
| 5,919,196 A | 7/1999 | Bobic et al. |
| 5,928,239 A | 7/1999 | Mirza |
| 5,928,286 A | 7/1999 | Ashby et al. |
| 5,964,752 A | 10/1999 | Stone |
| 5,964,768 A | 10/1999 | Huebner |
| 5,964,808 A | 10/1999 | Blaha et al. |
| 5,968,050 A | 10/1999 | Torrie |
| 5,989,269 A | 11/1999 | Vibe-Hansen et al. |
| 5,990,382 A | 11/1999 | Fox |
| 5,997,543 A | 12/1999 | Truscott |
| 5,997,582 A | 12/1999 | Weiss |
| 6,004,323 A | 12/1999 | Park et al. |
| 6,010,502 A | 1/2000 | Bagby |
| 6,015,411 A | 1/2000 | Ohkoshi et al. |
| 6,017,348 A | 1/2000 | Hart et al. |
| 6,019,767 A | 2/2000 | Howell |
| 6,045,564 A | 4/2000 | Walen |
| 6,052,909 A | 4/2000 | Gardner |
| 6,059,831 A | 5/2000 | Braslow |
| 6,071,310 A | 6/2000 | Picha et al. |
| 6,081,741 A | 6/2000 | Hollis |
| 6,086,593 A | 7/2000 | Bonutti |
| 6,102,948 A | 8/2000 | Brosnahan, III |
| 6,120,542 A | 9/2000 | Camino et al. |
| 6,132,433 A | 10/2000 | Whelan |
| 6,146,385 A | 11/2000 | Torrie et al. |
| 6,149,654 A | 11/2000 | Johnson |
| 6,159,216 A | 12/2000 | Burkinshaw et al. |
| 6,165,223 A | 12/2000 | Metzger et al. |
| 6,168,626 B1 | 1/2001 | Hyon et al. |
| 6,171,340 B1 | 1/2001 | McDowell |
| 6,193,724 B1 | 2/2001 | Chan |
| 6,206,885 B1 | 3/2001 | Ghahremani et al. |
| 6,217,549 B1 | 4/2001 | Selmon et al. |
| 6,217,619 B1 | 4/2001 | Keller |
| 6,235,060 B1 | 5/2001 | Kubein-Meesenburg |
| 6,251,143 B1 | 6/2001 | Schwartz et al. |
| 6,280,474 B1 | 8/2001 | Cassidy et al. |

| | | |
|---|---|---|
| 6,299,645 B1 | 10/2001 | Ogden |
| 6,299,648 B1 | 10/2001 | Doubler et al. |
| 6,306,142 B1 | 10/2001 | Johanson et al. |
| 6,315,798 B1 * | 11/2001 | Ashby et al. ............. 623/20.17 |
| 6,322,500 B1 | 11/2001 | Sikora et al. |
| 6,328,752 B1 | 12/2001 | Sjostrom et al. |
| 6,342,075 B1 | 1/2002 | MacArthur |
| 6,358,251 B1 | 3/2002 | Mirza |
| 6,358,253 B1 | 3/2002 | Torrie et al. |
| 6,375,658 B1 | 4/2002 | Hangody et al. |
| 6,383,188 B2 | 5/2002 | Kuslich |
| 6,415,516 B1 | 7/2002 | Tirado et al. |
| 6,443,954 B1 | 9/2002 | Bramlet et al. |
| 6,461,373 B2 | 10/2002 | Wyman et al. |
| 6,468,309 B1 | 10/2002 | Lieberman |
| 6,478,178 B2 | 11/2002 | Ralph et al. |
| 6,478,801 B1 | 11/2002 | Ralph et al. |
| 6,482,210 B1 | 11/2002 | Skiba et al. |
| 6,494,914 B2 | 12/2002 | Brown |
| 6,520,964 B2 | 2/2003 | Tallarida et al. |
| 6,527,754 B1 | 3/2003 | Tallarida et al. |
| 6,530,956 B1 | 3/2003 | Mansmann |
| 6,537,274 B1 | 4/2003 | Chibrac et al. |
| 6,540,786 B2 | 4/2003 | Chibrac et al. |
| 6,551,322 B1 | 4/2003 | Lieberman |
| 6,575,982 B1 | 6/2003 | Bonutti |
| 6,585,666 B2 | 7/2003 | Suh et al. |
| 6,591,581 B2 | 7/2003 | Schmieding |
| 6,599,321 B2 | 7/2003 | Hyde et al. |
| 6,607,561 B2 | 8/2003 | Brannon |
| 6,610,067 B2 | 8/2003 | Tallarida |
| 6,679,917 B2 | 1/2004 | Ek |
| 6,746,451 B2 | 6/2004 | Middleton et al. |
| 6,755,837 B2 | 6/2004 | Ebner |
| 6,770,078 B2 | 8/2004 | Bonutti |
| 6,783,550 B2 | 8/2004 | MacArthur |
| 6,783,551 B1 | 8/2004 | Metzger |
| 6,802,864 B2 * | 10/2004 | Tornier .................... 623/20.18 |
| 6,814,735 B1 | 11/2004 | Zirngibl |
| 6,827,722 B1 | 12/2004 | Schoenefeld |
| 6,860,902 B2 * | 3/2005 | Reiley .................... 623/21.18 |
| 6,884,246 B1 | 4/2005 | Sonnabend et al. |
| 6,923,813 B2 | 8/2005 | Phillips et al. |
| 6,926,739 B1 * | 8/2005 | O'Connor et al. ........ 623/21.18 |
| 6,962,577 B2 | 11/2005 | Tallarida et al. |
| 6,969,393 B2 | 11/2005 | Pinczewski et al. |
| 6,989,016 B2 | 1/2006 | Tallarida et al. |
| 7,029,479 B2 | 4/2006 | Tallarida |
| 7,063,717 B2 | 6/2006 | St. Pierre et al. |
| 7,115,131 B2 | 10/2006 | Engh et al. |
| 7,156,880 B2 | 1/2007 | Evans et al. |
| 7,160,305 B2 | 1/2007 | Schmieding |
| 7,163,541 B2 | 1/2007 | Ek |
| 7,166,133 B2 | 1/2007 | Evans et al. |
| 7,192,431 B2 | 3/2007 | Hangody et al. |
| 7,204,839 B2 | 4/2007 | Dreyfuss et al. |
| 7,204,854 B2 | 4/2007 | Guederian et al. |
| 7,235,107 B2 | 6/2007 | Evans et al. |
| 7,238,189 B2 | 7/2007 | Schmieding et al. |
| 7,241,316 B2 | 7/2007 | Evans et al. |
| 7,264,634 B2 | 9/2007 | Schmieding |
| 7,303,577 B1 | 12/2007 | Dean |
| 7,311,702 B2 | 12/2007 | Tallarida et al. |
| 7,510,558 B2 | 3/2009 | Tallarida |
| 7,569,059 B2 | 8/2009 | Cerundolo |
| 2001/0012967 A1 | 8/2001 | Mosseri |
| 2001/0039455 A1 | 11/2001 | Simon et al. |
| 2001/0056266 A1 | 12/2001 | Tallarida et al. |
| 2002/0055783 A1 | 5/2002 | Tallarida et al. |
| 2002/0106393 A1 | 8/2002 | Bianchi et al. |
| 2002/0138150 A1 | 9/2002 | Leclercq |
| 2002/0147498 A1 | 10/2002 | Tallarida et al. |
| 2003/0028196 A1 | 2/2003 | Bonutti |
| 2003/0060887 A1 | 3/2003 | Ek |
| 2003/0065391 A1 | 4/2003 | Re et al. |
| 2003/0105465 A1 | 6/2003 | Schmieding et al. |
| 2003/0120276 A1 | 6/2003 | Tallarida et al. |
| 2003/0120278 A1 | 6/2003 | Morgan et al. |
| 2003/0130741 A1 | 7/2003 | McMinn |
| 2003/0171756 A1 | 9/2003 | Fallin et al. |
| 2003/0181878 A1 | 9/2003 | Tallarida et al. |
| 2003/0204195 A1 | 10/2003 | Keane et al. |
| 2003/0216669 A1 | 11/2003 | Lang et al. |
| 2003/0225456 A1 | 12/2003 | Ek |
| 2003/0225457 A1 | 12/2003 | Justin et al. |
| 2004/0015170 A1 | 1/2004 | Tallarida et al. |
| 2004/0034359 A1 | 2/2004 | Schmieding et al. |
| 2004/0034437 A1 | 2/2004 | Schmieding |
| 2004/0082906 A1 | 4/2004 | Tallarida et al. |
| 2004/0106928 A1 | 6/2004 | Ek |
| 2004/0133276 A1 | 7/2004 | Lang et al. |
| 2004/0138754 A1 | 7/2004 | Lang et al. |
| 2004/0138758 A1 | 7/2004 | Evans et al. |
| 2004/0148030 A1 | 7/2004 | Ek |
| 2004/0153087 A1 | 8/2004 | Sanford et al. |
| 2004/0193281 A1 | 9/2004 | Grimes |
| 2004/0199166 A1 | 10/2004 | Schmieding et al. |
| 2004/0230315 A1 | 11/2004 | Ek |
| 2004/0260303 A1 | 12/2004 | Carrison |
| 2005/0015153 A1 | 1/2005 | Goble et al. |
| 2005/0038520 A1 | 2/2005 | Binette et al. |
| 2005/0043808 A1 | 2/2005 | Felt et al. |
| 2005/0065612 A1 | 3/2005 | Winslow |
| 2005/0075642 A1 | 4/2005 | Felt |
| 2005/0143731 A1 | 6/2005 | Justin et al. |
| 2005/0143745 A1 | 6/2005 | Hodorek et al. |
| 2005/0143831 A1 | 6/2005 | Justin et al. |
| 2005/0154398 A1 | 7/2005 | Miniaci et al. |
| 2005/0209705 A1 | 9/2005 | Niederauer et al. |
| 2005/0229323 A1 | 10/2005 | Mills et al. |
| 2005/0287187 A1 | 12/2005 | Mansmann |
| 2006/0004461 A1 | 1/2006 | Justin et al. |
| 2006/0020343 A1 | 1/2006 | Ek |
| 2006/0052878 A1 | 3/2006 | Schmieding |
| 2006/0058744 A1 | 3/2006 | Tallarida et al. |
| 2006/0085006 A1 | 4/2006 | Ek |
| 2006/0149370 A1 | 7/2006 | Schmieding et al. |
| 2006/0190002 A1 | 8/2006 | Tallarida |
| 2006/0195112 A1 | 8/2006 | Ek |
| 2006/0229726 A1 | 10/2006 | Ek |
| 2007/0005143 A1 | 1/2007 | Ek |
| 2007/0073394 A1 | 3/2007 | Seedhom et al. |
| 2007/0093842 A1 | 4/2007 | Schmieding |
| 2007/0093890 A1 | 4/2007 | Eliasen et al. |
| 2007/0118136 A1 | 5/2007 | Ek |
| 2007/0123921 A1 | 5/2007 | Ek |
| 2007/0179608 A1 | 8/2007 | Ek |
| 2007/0233128 A1 | 10/2007 | Schmieding et al. |
| 2007/0250067 A1 | 10/2007 | Schmieding et al. |
| 2007/0255399 A1 | 11/2007 | Eliasen et al. |
| 2007/0265700 A1 | 11/2007 | Eliasen et al. |
| 2007/0288031 A1 | 12/2007 | Dreyfuss et al. |
| 2007/0299519 A1 | 12/2007 | Schmieding |
| 2008/0004659 A1 | 1/2008 | Burkhart et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0086139 A1 | 4/2008 | Bourke et al. |
| 2008/0172125 A1 | 7/2008 | Ek |
| 2008/0183290 A1 | 7/2008 | Baird et al. |
| 2008/0188935 A1 | 8/2008 | Saylor et al. |
| 2008/0275512 A1 | 11/2008 | Albertirio et al. |
| 2008/0306483 A1 | 12/2008 | Iannarone |
| 2009/0198288 A1 | 8/2009 | Hoof et al. |

| | | |
|---|---|---|
| 2009/0234452 A1 | 9/2009 | Steiner et al. |

FOREIGN PATENT DOCUMENTS

| | | |
|---|---|---|
| AU | 2003262428 | 8/2009 |
| DE | 2933174 | 4/1980 |
| DE | 3516743 | 11/1986 |
| EP | 0350780 | 7/1989 |
| EP | 0350780 | 1/1990 |
| EP | 0485678 | 5/1992 |
| EP | 0327387 | 9/1992 |
| EP | 0505634 | 9/1992 |
| EP | 0903125 | 3/1999 |
| EP | 0903127 | 3/1999 |
| EP | 0661023 | 8/2001 |
| EP | 1426013 | 9/2004 |
| EP | 1278460 | 4/2009 |
| FR | 2242068 | 3/1975 |
| FR | 2642301 | 3/1990 |
| FR | 2676917 | 12/1992 |
| FR | 2718014 | 10/1995 |
| FR | 2739151 | 3/1997 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2002291779 | 10/2002 |
| JP | 2003534096 | 11/2003 |
| WO | WO8803781 | 6/1988 |
| WO | 8909578 | 10/1989 |
| WO | 9427507 | 12/1994 |
| WO | 9624304 | 8/1996 |
| WO | WO9722306 | 6/1997 |
| WO | 9920192 | 4/1999 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 2004014261 | 2/2004 |
| WO | 2004026170 | 4/2004 |
| WO | 2004075777 | 9/2004 |
| WO | 2005051231 | 6/2005 |
| WO | WO2005051231 | 6/2005 |
| WO | 2006004885 | 1/2006 |
| WO | 2006091686 | 8/2006 |

OTHER PUBLICATIONS

International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
International Search Report and Written Opinion dated Aug. 8, 2007 issued in corresponding PCT patent application No. PCT/US06/29875.
Notice of Allowance issued in corresponding U.S. Appl. No. 10/308,718, dated Sep. 11, 2006.
Office Action issued in corresponding U.S. Appl. No. 11/326,133, dated Oct. 17, 2007.
Office Action issued in corresponding U.S. Appl. No. 10/741,044, dated Oct. 26, 2005.
USPTO Office Action dated Dec. 21, 2007 issued in corresponding U.S. Appl. No. 11/169,326.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.

USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application no. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
United States Office Action issued is related U.S. Appl. No. 10/760,965, dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
Habermeyer, Peter, ATOS News, "The artificial limb" Eclipse"A new draft without shank in the implantation of artificial shoulder limb", Jan. 13, 2006 (5 pages).
Suganuma, et al., "Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).
Siguier, et al., "Preliminary Results of Partial Surface Replacement of the Femoral Head in Osteonecrosis", The Journal of Arthroplasty, vol. 14, No. 1, 1999 (7 pages).
Siguier, et al., "Partial Resurfacing Arthroplasty of the Femoral Head in Avascular Necrosis", Clinical Orthopaedics and Related Research, No. 386, pp. 85-92, 2001 (5 pages).
International Search Report with Written Opinion dated Aug. 30, 2006 received in corresponding PCT Application No. PCT/US06/06323 (11 pages).
Examination Report dated Feb. 22, 2005 received in corresponding European Application No. 01 932 833.5 (3 pages).
Examination Report dated Mar. 15, 2005 received in corresponding European Application No. 03 026 286.9 (3 pages).
International Search Report dated May 23, 2003 received in corresponding PCT Application No. PCT/US02/40310 (6 pages).
International Search Report dated Nov. 12, 2002 recevied in corresponding PCT Application No. PCT/US01/48821 (9 pages).
International Search Report dated Dec. 27, 2001 received in corresponding PCT Application No. PCT/US01/14061 (5 pages).
Thermann, et al, ATOS Newsletter, Jun. 2005, Aktuelle Themen, (16 pages).
Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
Cannulated Hemi Implants from Vielex, (3 pages).
APTA | Knee,/http://www.apta.org/AM/PrinerTemplate.cfm?Section=Home&Template=/CM/HTMLDisplay.dfg& . . . Jun. 25, 2007 (1page).
Arthrosurface, Restoring the Geometry of Motion, HemiCAP Patello—Femoral Resurfacing System (19 pages).
Anatomical Arthroplastie, Total Evolutive Shoulder System T.E.S.S., Biomet France, Biomet Europe (4 pages).
American Machinist, Full-radius milling cutters, http://www.americanmachinist.com/Classes/Article/ArticleDraw__P. aspx, Jun. 26, 2007 (1 page).
Chuck (engineering),Wikipedia, the free encyclopedia, http://en.wikipedia.org/w/index.php?title=Chuck_% 28engineering%29&printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Major Biojoint System, La nuova frontiera della biointegrazione naturale, Finceramica Biomedical solutions (4 pages).
Makita Industrial Power Tools, Product Details Print Out, Chain Mortiser, http://www.makita.com/menu.php?pg=product__det__prn&tag=7104L, Jun. 26, 2007 (3pgs).
Milling machine, Wikipedia, the free encyclopedia, http://en.wikipedia.org/w/index.php?title=Milling__machine&printable=yes, Jun. 26, 2007 (4 pages).
Mortise and tenon, Wikipedia, the free encyclopedia, http://en.wikipedia.org/w/index.php?title=Mortise__and__tenon&printable=yes, Jun. 25, 2007 (3 pages).
Oka et al, "Development of artificial articular cartilage", Proc Instn Mech Engrs vol. 214 Part H, 2000 pp. 59-68 (10 pages).
Reversed Arthroplastie, Total Evolutive Shoulder System T.E.S.S., Biomet France, Biomet Europe (4 pages).
The Mini Uni: A New Solution for Arthritic Knew Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral hear", An Experimantal Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw__angle&printable=yes, Jun. 25, 2007 (1 page).
Bale, MD, Reto J., et al, "Osteochondral Lesions of the Talus: Computer=assisted Retrograde Drilling Feasibility and Accuracy in Initial Experriences[1]", (Radiology. 2001;218:278-282) © RSNA, 2001.

Biomet/Copeland, "Aequalis® Resurfacing Head" Tornier, Scientific Vision, Surgical Leadership, SS-401 Jan. 2007.

Kumai, M.D., Tsukasa, et al Arthroscopic Drilling for the Treatment of Osteochondral Lesions of the Talus, the Journal of Bone & Joint Surgery, American vol. 81:1229-35(1999).

Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 (Jul.-Aug.), 2001:pp. 653-659.

Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.

Schneider, T., et al, "Arthroscopy of the ankle joint. A list of indications and realistic expectations", Foot and Ankle Surgery 1996 2:189-193, © 1996 Arnette Blackwell SA.

Taranow WS, et al, "Retrograde drilling of osteochondral lesions of the medial talar dome", PubMed, www.pubmed.gov, A service of the National Library of Medicing and the Natinal Institutes of Health, Foot Ankle Int.Aug. 1999; 20 (8):474-80.

Ueblacker, M.D., Peter, et al, "Retrograde Cartilage Transplantation of the Proximal and Distal Tibia", Arthroscopy: The Journal of Arthroscipic and Related Surgery, vol. 20, No. 1 (Jan.), 2004: pp. 73-78.

European Communication pursuant to Article 96)2) EPC dated Sep. 11, 2006 received in corresponding European Patent Application Serial No. 01 932 833.5 (3 pages).

U.S. Office Action dated Jan. 9, 2009 issued in related U.S. Appl. No. 10/373,463.

Canadian Office Action dated Dec. 9, 2008 issued in related Canadian Patent Application No. 2407440.

Supplemental European Search Report dated Nov. 6, 2008 issued in related European Patent Application No. 05791453.3-2310.

Japanese Office Action dated Dec. 19, 2008 issued in Japanese Patent Application No. 2006501193.

Japanese Office Action dated Jan. 13, 2009 issued in Japanese Patent Application No. 2003552147.

International Search Report dated Jan. 30, 2006 issued in related International Patent Application No. PCT/US04/39181.

U.S. Office Action dated Mar. 27, 2009 issued in related U.S. Appl. No. 11/169,326.

European Office Action dated Feb. 26, 2009 in related European Patent Application No. 05791453.3.

U.S. Office Action issued in related U.S. Appl. No. 11/326,133 dated Jun. 12, 2008.

International Search Report and Written Opinion dated Jun. 24, 2008 issued in related International Patent Application No. PCT/US07/73685.

International Search Report and Written Opinion dated Jun. 11, 2008 issued in related International Patent Application No. PCT/US07/25284.

International Search Report and Written Opinion dated Aug. 8, 2008 issued in related International Patent Application No. PCT/US08/53988.

U.S. Office Action issued in related U.S. Appl. No. 10/994,453 dated Jun. 5, 2007.

Japanese Office Action dated Jul. 22, 2008 issued in related Japanese Patent Application No. 2006-501193.

U.S. Office Action issued in related U.S. Appl. No. 10/373,463 dated Apr. 21, 2008.

Notice of Allowance received in U.S. Appl. No. 10/618,887 dated Aug. 15, 2008.

Australia Office Action issued in related Australian Patent Application No. 2007216648 dated May 30, 2008.

European Office Action issued in related European Patent Application No. 01932833.5-2310 dated Apr. 25, 2008.

U.S. Office Action received in related U.S. Appl. No. 11/169,326 dated Jun. 30, 2008.

U.S. Office Action received in related U.S. Appl. No. 11/169,326 dated Jul. 27, 2007.

U.S. Office Action received in related U.S. Appl. No. 11/169,326 dated Apr. 17, 2007.

U.S. Office Action received in related U.S. Appl. No. 11/169,326 dated Mar. 9, 2007.

Canadian Office Action issued in related Canadian Patent Application No. 2546582 dated Aug. 21, 2008.

U.S. Office Action issued in related U.S. Appl. No. 10/994,453 dated Sep. 3, 2008.

U.S. Office Action dated Oct. 21, 2008 issued in related U.S. Appl. No. 11/461,240.

Habermeyer, "Eclipse, Schaftfreie Schulterprothese Operationsanleitung," (dated unknown).

U.S. Office Action dated Sep. 25, 2008 issued in related U.S. Appl. No. 11/326,133.

U.S. Office Action dated Jul. 2, 2008 issued in related U.S. Appl. No. 11/379,151.

European Office Action dated Oct. 6, 2008 issued in related European Patent Application No. 01932833.5-2310.

U.S. Office Action dated Jun. 27, 2008 issued in related U.S. Appl. No. 10/760,965.

International Search Report and Written Opinion dated Oct. 1, 2008 issued in related International Patent Application No. PCT/US08/53194.

International Search Report and Written Opinion dated Oct. 9, 2008 issued in related International Patent Application No. PCT/US07/82262.

European Search Report dated Nov. 4, 2008 issued in related European Patent Application No. 04811836.8-2310.

Mccarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).

Bushnell, et al., "Bony Instability of the Shoulder," Arthroscopy, The Journal of Arthroscopic and related Surgery, vol. 24, No. 9; Sep. 2005 (pp. 1061-1073).

Scalise, et al., "Resurfacing Arthroplasty of the Humerus: Indications, Surgical Technique, and Clinical Results," Techniques in Shoulder and Elbow Surgery 8(3):152-160; 2007.

Davidson, et al., "Focal Anatomic Patellofemoral Inlay Resurfacing: Theoretic Basis, Surgical Technique, and Case Reports," Orthop. Clin. N. Am., 39 (2008) pp. 337-346.

Provencher, et al., "Patellofemoral Kinematics After Limited Resurfacing of the Trochlea," The Journal of Knee Surgery, vol. 22 No. 2 (2008) pp. 1-7.

Dawson, et al., "The Management of Localized Articular Cartilage Lesions of the Humeral Head in the Athlete," Operative Techniques in Sports Medicine, vol. 16, Issue 1, pp. 14-20 (2008).

Uribe, et al., "Partial Humeral Head Resurfacing for Osteonecrosis," Journal of Shoulder and Elbow Surgery, (2009) 6 pages.

Burks, "Implant Arthroplasty of the First Metatarsalphalangeal Joint," Clin. Podiatr. Med. Surg., 23 (2006) pp. 725-731.

Hasselman, et al., "Resurfacing of the First Metatarsal Head in the Treatment of Hallux Rigidus," Techniques in Foot & Ankle Surgery 7(1):31-40, 2008.

Gelenkoberflachen, et al., "Partial hemi-resurfacing of the hip joint—a new approach to treat local osteochondral defects?" Biomed Tech 2006; 51:371-376 (2006).

Sullivan, "Hallux Rigidus: MTP Implant Arthroplasty," Foot Ankle Clin. N. Am. 14 (2009) pp. 33-42.

Cook, et al., "Meta-analysis of First Metatarsophalangeal Joint Implant Arthroplasty," Journal of Foot and Ankle Surgery, vol. 48, Issue 2, pp. 180-190 (2009).

Derner, "Complications and Salvage of Elective Central Metatarsal Osteotomies," Clin. Podiatr. Med. Surg. 26 (2009) 23-35.

Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.

Beecher, et al. "Effects of a contoured articular prosthetic device on tibiofemoral peak contact pressure: a biomechanical study," Knee Surg Sports Traumatol Arthrosc. Jan. 2008; 16(1): 56-63.

United States Office Action dated May 13, 2009 issued in related U.S. Appl. No. 11/359,892.

United States Office Action dated May 18, 2009 issued in related U.S. Appl. No. 11/209,170.

United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
Notice of Reasons for Rejection issued in related Japanese Patent Application No. 2003-394702 mailed Jul. 21, 2009.
Notice of Reasons for Rejection issued in related Japanese Patent Application No. 20-541615 mailed May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 18, 2009 issued in related U.S. Appl. No. 11/209,170.
Notice of Allowance dated Feb. 20, 2009 issued in related U.S. Appl. No. 10/618,887.
U.S. Office Action dated May 13, 2009 issued in related U.S. Appl. No. 11/359,892.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
International Preliminary Report on Patentability dated Aug. 20, 2009 issued in related International Patent Application No. 2008053194.
Notice of Allowance dated August 27, 2009 issued in related U.S. Appl. No. 10/760,965.
Notice of Allowance dated August 25, 2009 issued in related U.S. Appl. No. 11/379,151.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
International Preliminary Report on Patentability dated Aug. 20, 2009 issued in related International Patent Application No. PCT/US2008/053194.
Australian Notice of Allowance dated Oct. 29, 2009 issued in related Australian Patent Application No. 2007216648.
Notice of Allowance dated Aug. 27, 2009 issued in related U.S. Appl. No. 10/760,965.
Notice of Allowance dated Oct. 9, 2009 issued in related U.S. Appl. No. 10/373,463.
Australian Office Action dated Oct. 29, 2009 issued in related Australian Patent Application No. 2007203623.
Notice of Allowance dated Aug. 25, 2009 issued in related U.S. Appl. No. 11/379,151.
Japanese Notice of Reasons for Rejection dated Sep. 8, 2009 issued in related Japanese Patent Application No. 2003552147.
Notice of Reasons for Rejection dated Nov. 17, 2009 issued in Japanese Patent Application No. 2007-519417.
European Search Report dated Dec. 3, 2009 issued in related European Patent Application No. 06735827.5.
U.S. Office Action dated Jan. 25, 2010 issued in related U.S. Appl. No. 11/326,113.
Supplemental Notice of Allowance dated Nov. 25, 2009 issued in related U.S. Appl. No. 10/373,463.
Office Action dated Dec. 24, 2009 issued in related U.S. Appl. No. 10/994,453.
European Office Action dated Jan. 11, 2010 issued in related European Patent Application No. 2005218302.

* cited by examiner

ARTICULAR SURFACE IMPLANT

CROSS REFERENCE TO RELATED APPLICATIONS

This application claims the benefit of U.S. provisional patent application Ser. No. 60/654,989, filed Feb. 22, 2005. This application is also a continuation-in-part of U.S. patent application Ser. No. 10/373,463, filed Feb. 24, 2003 which is a continuation-in-part application of application Ser. No. 10/162,533, filed Jun. 4, 2002, now U.S. Pat. No. 6,679,917 which is itself a continuation-in-part application of application Ser. No. 10/024,077, filed Dec. 17, 2001, now U.S. Pat. No. 6,610,067 which is itself a continuation-in-part application of application Ser. No. 09/846,657, filed May 1, 2001, now U.S. Pat. No. 6,520,964 which claims priority from U.S. provisional application Ser. No. 60/201,049, filed May 1, 2000, all of which are incorporated herein for reference. The entire disclosures of all of the above-identified applications are incorporated herein by reference.

FIELD

The present disclosure is directed at a system and method for accessing an articular joint surface. The present disclosure is further directed at a method and system for replacing at least a portion of an articular surface.

BACKGROUND

Articular cartilage, found at the ends of articulating bone in the body, is typically composed of hyaline cartilage, which has many unique properties that allow it to function effectively as a smooth and lubricious load bearing surface. Hyaline cartilage problems, particularly in knee, hip joints, and should joints, are generally caused by disease such as occurs with rheumatoid arthritis or wear and tear (osteoarthritis), or secondary to an injury, either acute (sudden), or recurrent and chronic (ongoing). Such cartilage disease or deterioration can compromise the articular surface causing pain and eventually, loss of joint movement. As a result, various methods have been developed to treat and repair damaged or destroyed articular cartilage.

For smaller defects, traditional options for this type of problem include leaving the lesions or injury alone and living with it, or performing a procedure called abrasion arthroplasty or abrasion chondralplasty. The principle behind this procedure is to attempt to stimulate natural healing. The bone surface is drilled using a high speed rotary burr or shaving device and the surgeon removes about 1 mm of bone from the surface of the lesion. This creates an exposed subchondral bone bed that will bleed and will initiate a fibrocartilage healing response. One problem with this procedure is that the exposed bone is not as smooth as it originally was following the drilling and burring which tends to leave a series of ridges and valleys, affecting the durability of the fibrocartilage response. Further, although this procedure can provide good short term results, (1-3 years), fibrocartilage is seldom able to support long-term weight bearing and is prone to wear, soften and deteriorate.

Another procedure, called Microfracture incorporates some of the principles of drilling, abrasion and chondralplasty. During the procedure, the calcified cartilage layer of the chondral defect is removed. Several pathways or "microfractures" are created to the subchondral bleeding bone bed by impacting a metal pick or surgical awl at a minimum number of locations within the lesion. By establishing bleeding in the lesion and by creating a pathway to the subchondral bone, a fibrocartilage healing response is initiated, forming a replacement surface. Results for this technique may be expected to be similar to abrasion chondralplasty.

Another means used to treat damaged articular cartilage is a cartilage transplant. Essentially, this procedure involves moving cartilage from an outside source or other knee or from within the same knee into the defect. Typically, this is done by transferring a peg of cartilage with underlying bone and fixing it in place with a screw or pin or by a press fit. Although useful for smaller defects, large defects present a problem, as this procedure requires donor pegs proportionate to the recipient bed. Large diameter lesions may exceed the capacity to borrow from within the same knee joint and rule out borrowing from another source.

Larger defects, however, generally require a more aggressive intervention. Typically treatment requires replacing the articular surface with an implant or prosthetic having an outer layer that that is polished or composed of a material that provides a lubricious load bearing surface in approximation of an undamaged cartilage surface. Replacement of the articular surface requires first cutting, boring, or reaming the damaged area to remove the damaged cartilage. A recess to receive an implant or prosthetic is formed at the damaged site. The implant or prosthetic is then secured to the bone in an appropriate position in the recess.

BRIEF DESCRIPTION OF THE DRAWINGS

The subject matter of the present disclosure is set forth by description of embodiments consistent therewith, which description should be considered in combination with the accompanying drawings, wherein.

DESCRIPTION

Figure 1:
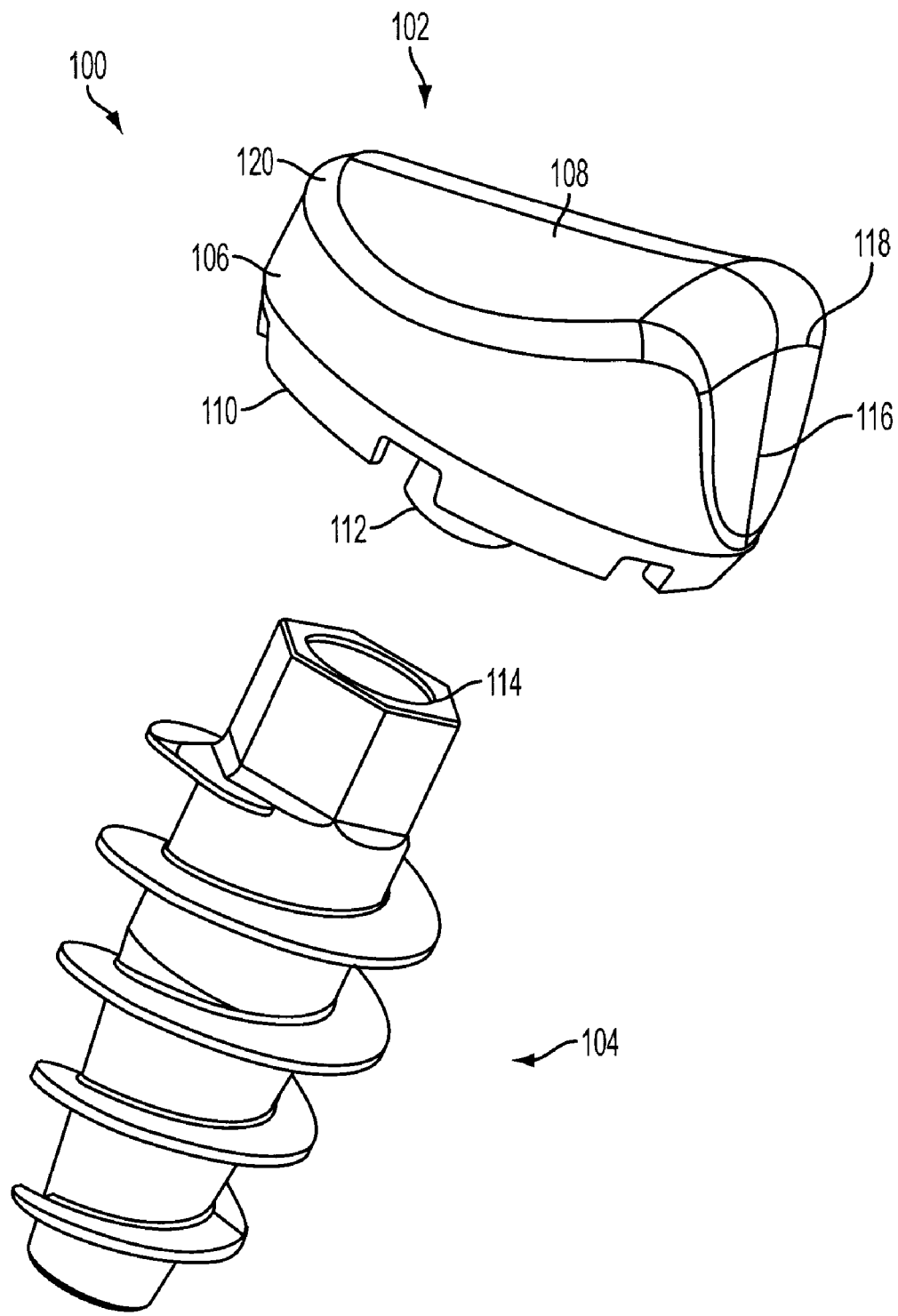
FIG. 1 is an exploded perspective view of an embodiment of an implant system including an implant consistent with the present disclosure and a fixation element that may be used in conjunction with the implant.
Figure 2:
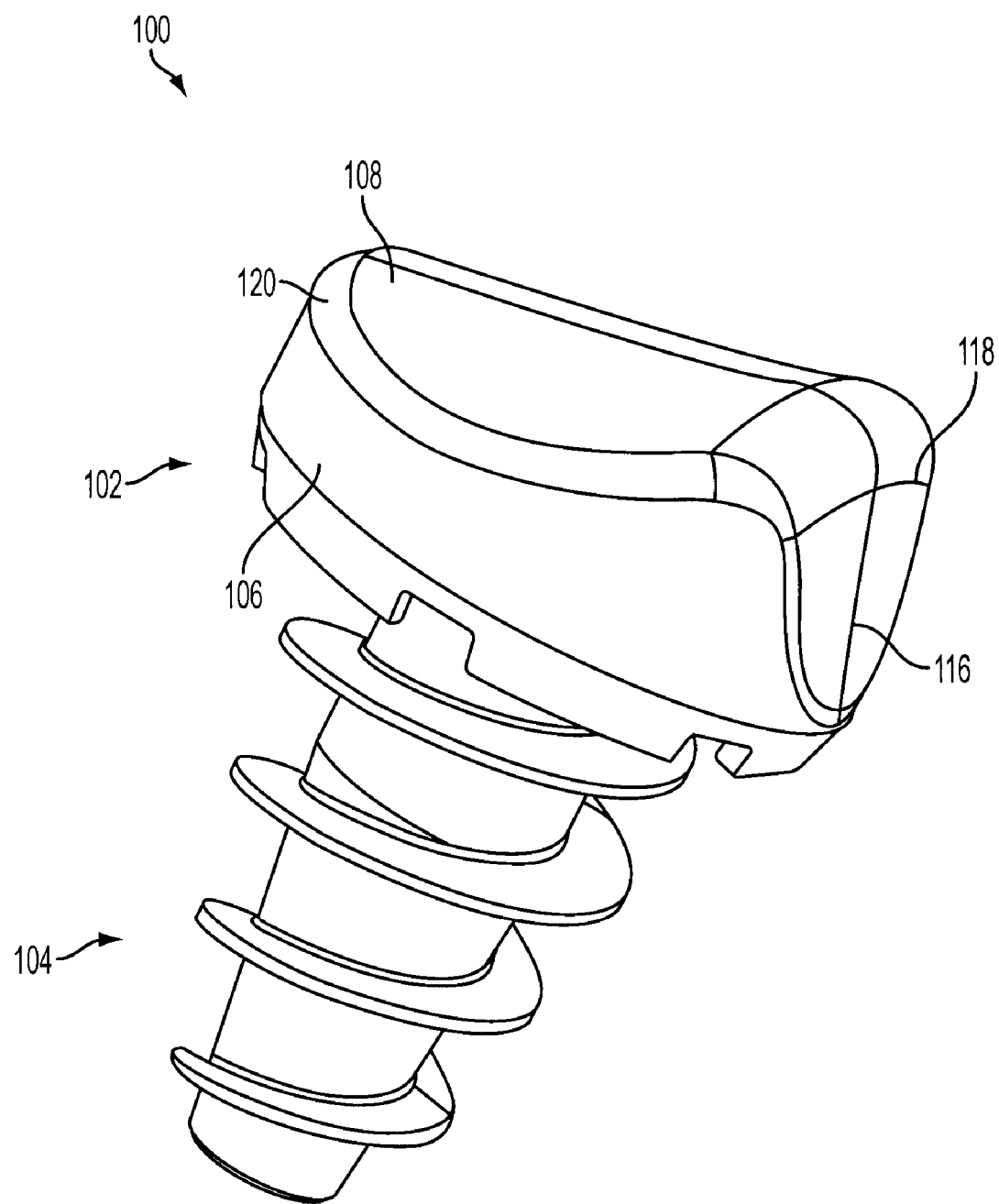
FIG. 2 is a perspective view of the embodiment of an implant system shown in FIG. 1 showing the implant assembled to the fixation element.

By way of overview, the present disclosure may provide an implant for replacing at least a portion of an articular surface. Furthermore, the present disclosure is also directed at a general design methodology for developing and producing a surface contour of an implant for replacing at least a portion of an articular surface. An implant consistent with the present disclosure may be provided having a load-bearing surface that is adapted to interact with a cooperating articulating feature. The cooperating articulating feature may include, for example, a cooperating articular surface, a cooperating surface of an implant replacing at least a portion of a cooperating articular surface, etc. In one embodiment, a portion of an articular surface to be replaced by an articular surface implant herein may be identified and replaced using a minimally invasive surgical procedure, for example, using diagnostic and/or surgical arthroscopy procedures. Generally, an implant according to the present disclosure may have a load bearing surface that may be based on an original geometry of an articular surface to be replaced by the implant.

Referring to FIGS. 1 through 4, an embodiment of an implant system 100 is schematically depicted in various views. The implant system 100 may be employed to replace at least a portion of an articular surface, e.g., at least a portion of an articular surface of a joint. As shown, the implant system 100 may generally include an articular surface implant 102 and a fixation element 104. The fixation element 104 may be capable of coupling the implant 102 to bone and/or other tissue in the region of the portion of the articular surface to be replaced by the implant 102. As shown in the illustrated embodiment of FIG. 1, the fixation element 104 may be provided as a separate component from the implant 102. In such an embodiment, the fixation element 104 may be capable of being coupled to the implant 102 and may be capable of being coupled to bone and/or tissue in the general region of the portion of the articular surface to be replaced by the implant system 100.

The articular surface implant 102 may generally include an implant body 106. The implant body 106 may have a load bearing surface 108 and a bone contacting region 110. The load bearing surface 108 may generally be configured to interact with a cooperating articulating feature, such as a cooperating articular surface, a cooperating articular surface implant, etc. In one embodiment, the implant body 106 may be at least partially received in an implant site provided by excising at least a portion of the articular surface and underlying bone. In such an embodiment, the load bearing surface 108 may be disposed generally replacing at least a portion of the excised articular surface. In an embodiment herein, the bone contacting region 110 may engage and/or contact subchondral within and/or forming at least a portion of a bottom of the implant site.

As mentioned previously, and consistent with the illustrated embodiment, the fixation element 104 maybe provided as a separate component from the implant 102. Providing the fixation element 104 as a separate component from the implant 102 may facilitate installation of the implant system 100. The fixation element 104 may first be coupled to bone and/or other tissue in and/or around the implant site. The implant 102 may then be positioned relative to the surrounding articular surface and the implant 102 may be coupled to the fixation element 104. In such a manner, the implant 102 may be secured in position relative to the articular surface.

In the illustrated embodiment, the fixation element 104 is depicted as a screw-type feature. Consistent with this illustrated embodiment, the fixation element 104 may be threadably engaged with bone and/or other tissue in and/or around the implant site. In addition to engaging bone and/or other tissue, a screw-type fixation element 104 may also facilitate depth positioning of the fixation element 104, and thereby depth positioning of the implant 102, relative to the articular surface. Suitable screw-type fixation elements are known in the art, for example, from U.S. Pat. No. 6,520,964, issued on Feb. 18, 2003. Consistent with various alternative embodiments, the fixation element may be configured having a barbed member or other similar features capable of engaging bone and/or other tissue in and/or around the implant site. In still other embodiments, the fixation element may include features that may be adhesively coupled to bone and/or other tissue in and/or around the implant site.

As illustrated, in an embodiment consistent with the present disclosure, the implant 102 and the fixation element 104 may be provided as separate components. The implant 102 may be coupled to the fixation element 104 to, at least in part, secure the implant 102 in position in the implant site. The implant 102 and the fixation element 104 may, accordingly, include interacting features wherein the implant 102 and fixation element 104 are capable of being coupled to one another. An embodiment of an implant 102 may be provided including a post 112 extending from the implant body 106. The fixation element 104 may include an opening 114 capable of receiving at least a portion of the post 112. In one such embodiment, the post 112 and the opening 114 may be provided having complimentary precision tapers. The implant 102 and the fixation element 104 may be coupled to one another by inserting the post 112 into the opening 114 and pressing the features together, e.g., as by applying an impact force. The precision taper of the post 112 and the opening 114 may achieve a secure frictional interaction between the implant 102 and the fixation element 104.

Various additional and/or alternative features and/or arrangements may be utilized for coupling the implant and the fixation element within the context of the present disclosure. Furthermore, in various embodiments in which the implant and the fixation element are provided as separate components, the implant and the fixation element may be assembled to one another prior to installation into an implant site. Consistent with some such embodiments, the fixation element may be configured to engage and/or to be coupled to bone and/or tissue in and/or around the implant site during installation. In one such embodiment, the fixation element may include a barbed post or similar feature. According to still further embodiments, the implant and the fixation element may be provided as a unitary structure.

The illustrated implant system 100 depicted in FIGS. 1 through 7 shows an implant 102 configured to replace a portion of the articular surface of the talus. Particularly, the illustrated implant system 100 shown in FIGS. 1 through 7 is configured to replace at least a portion of the lateral ridge of the trochlear surface of the talus, which articulates with the tibia. Damage to the lateral ridge of the trochlear surface of the talus may include fracture or shearing off of a portion of the ridge resulting from trauma. From a general perspective, the load bearing surface 108 may have a contour and/or geometry that may be capable of cooperating with an interacting articulating feature, including a cooperating articular surface, at least a portion of an implant replacing at least a portion of a cooperating articular surface, etc. In the context of the illustrated embodiment, the load bearing surface 108 may have a contour and/or geometry that may be capable of cooperating with an interacting articular surface of a tibia. According to a related embodiment in the context of the illustrated embodiment, the load bearing surface 108 of the implant 102 may include a geometry and/or contour that may be capable of cooperating with an interacting surface of an implant replacing at least a portion of an articular surface of a tibia.

Consistent with the foregoing, an implant may include a load bearing surface having a contour and/or geometry that may be capable of cooperating with an interacting articulating surface. In one embodiment, the load bearing surface may have a contour and/or geometry that may generally approximate and/or be based on a contour and/or geometry of the portion of the articular surface being replaced by the implant. In an embodiment, the portion of the articular surface being replaced may be mapped using various know techniques to quantitatively and/or qualitatively assess the contour and/or geometry of the portion of the articular surface that may be replaced by the implant. An implant may be constructed and/or selected from a set of implants having various contours and/or geometries. Consistent with such an embodiment, the load bearing surface of the implant may be based on the contour and/or geometry of the portion of the articular surface to be replaced by the implant. In an alternative embodiment, an implant may be fabricated or selected from a set of standard size and/or shape implants to provide a general approximation of the articular surface being replaced. Selection and/or fabrication of an implant may rely on various degrees of quantitative reference to the articular surface being replaced, including no quantitative reference to the articular surface.

Referring to FIGS. 1 through 4, according to one aspect, a contour and/or geometry of the load bearing surface 108 of an implant 102 may generally be defined by a first curve string 116 and a second curve string 118. As used in any embodiment herein, a curve string may include a single curve and/or a plurality of curves joined together curves in a plane. The first curve string 116 and the second curve string 118 generally defining the contour and/or geometry of the load bearing surface 108 may be disposed in intersecting planes. In the illustrated embodiment, the plane of the first curve string 116 and the plane of the second curve string 118 may generally be mutually perpendicular. Various other angular relationships of the planes including the first curve string 116 and the second curve string 118 may also suitably be employed herein.

A design methodology capable of achieving a load bearing surface of an implant herein may include providing a curve string defining a contour and/or geometry of the load bearing surface and sweeping the curve string along another curve string defining an intersecting contour and/or geometry of the load bearing surface. As alluded to above, curve strings defining the contour and/or geometry of the load bearing surface may be derived based on mapped curves and/or approximations of curves of a portion of an articular surface to be replace, a portion of a cooperating articulating feature, etc. In one such embodiment, measurements of the contour and/or geometry of the portion of the articular surface to be replaced may be taken. Measurement of the contour and/or geometry of the portion of the articular surface to be replaced by the implant may be achieved using direct contact contour mapping of the articular surface, e.g., measuring relative heights of various regions of the articular surface, and/or using various imaging techniques, such as radiological imaging techniques.

Figure 3:
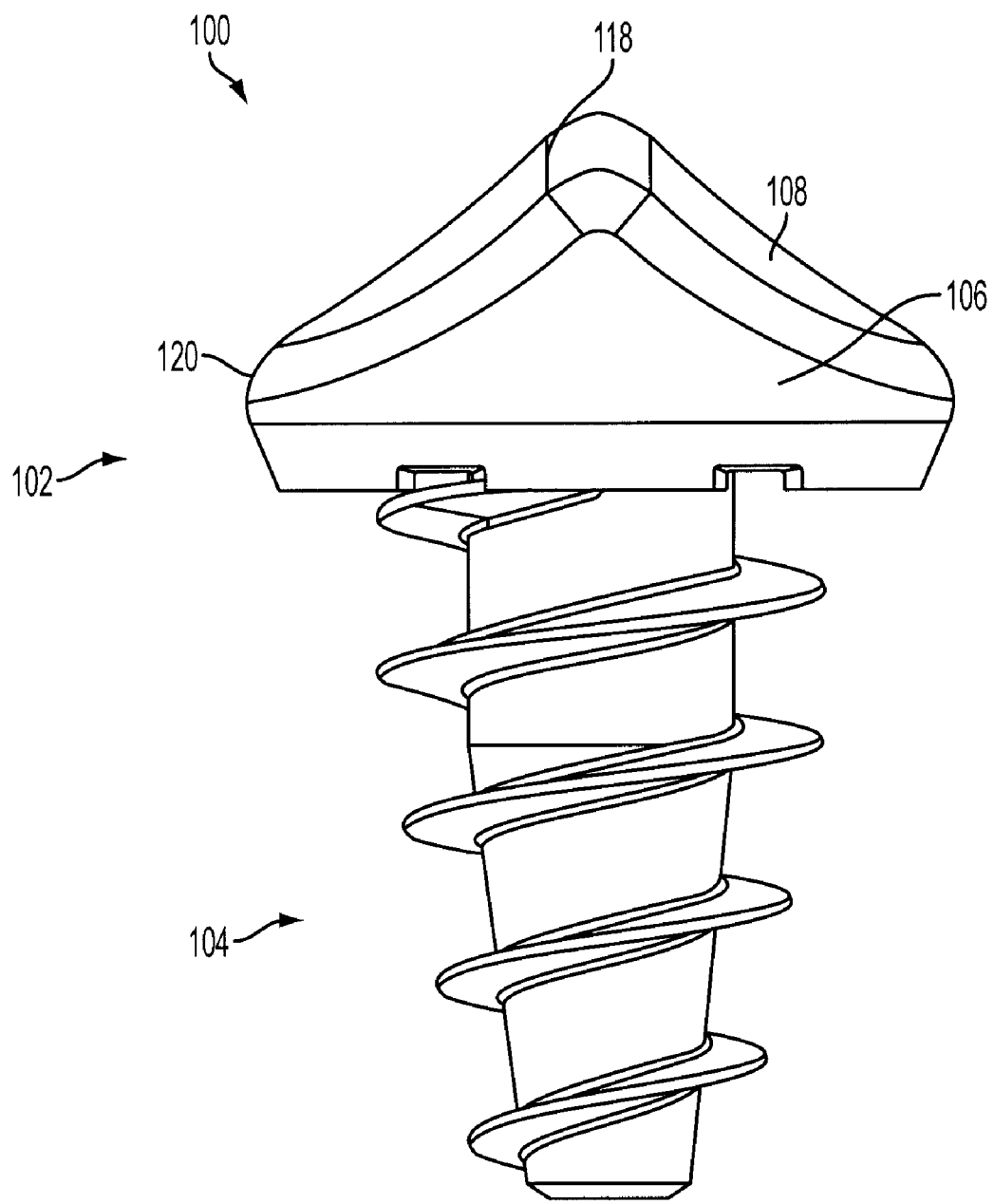
FIG. 3 is a perspective view of another embodiment of an implant system consistent with the present disclosure including an implant and a fixation element.
Figure 4:
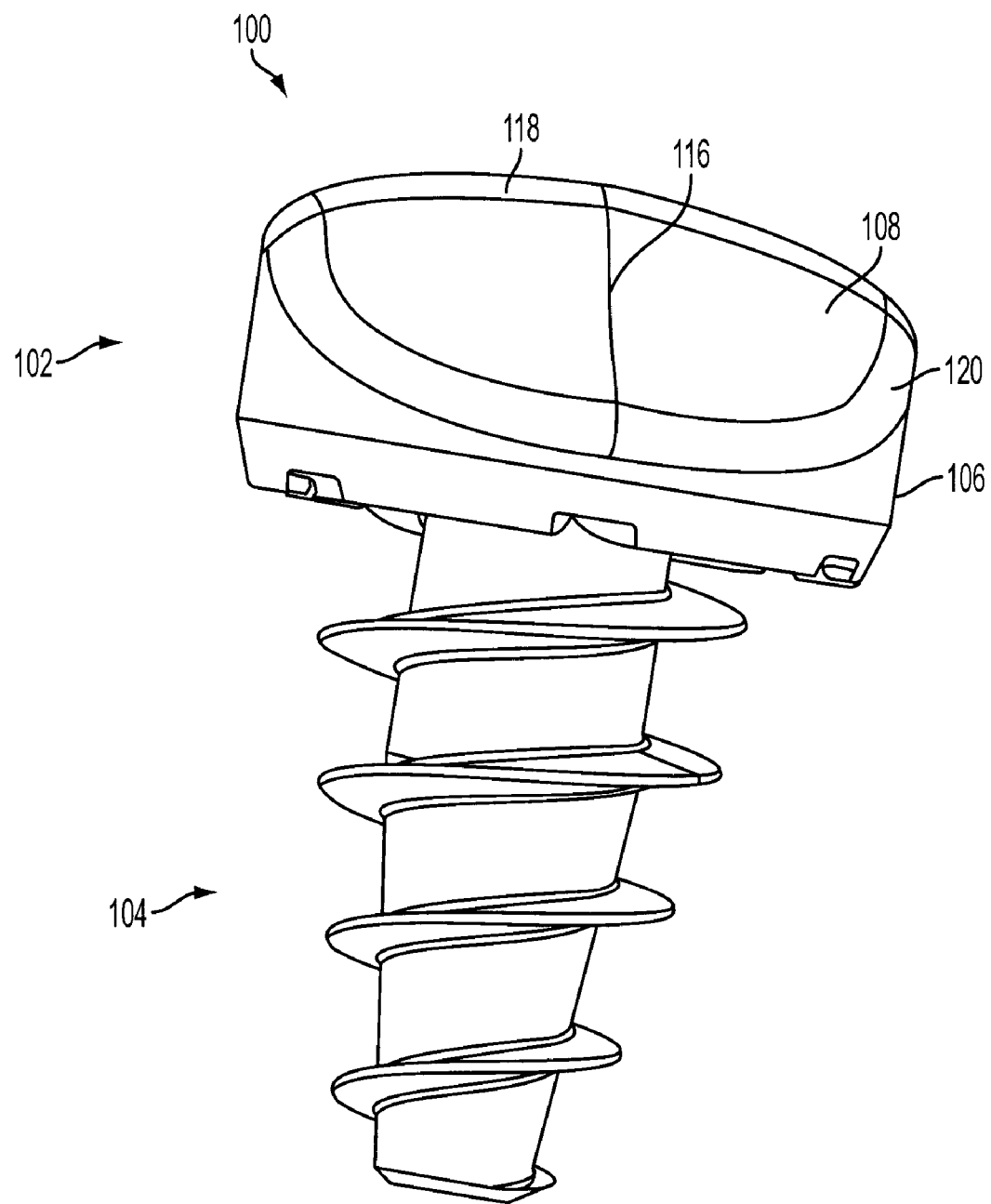
FIG. 4 illustrates the implant system shown in FIG. 3 from another perspective.

According to one embodiment, the load bearing surface 108 may have a contour and/or geometry corresponding to the second curve string 118 lofted over the first curve string 116. In one such embodiment, the contour and/or geometry of the load bearing surface 108 may be achieved by sweeping the second curve string 118 along the first curve 116 while maintaining the second curve 118 normal to the first curve 116. In such an embodiment, the first curve 116 may be provided in a first plane, e.g. a plane defined by the X and Z axis. The second curve 118 may be provided in a perpendicular plane. The angular pitch of the perpendicular plane relative to the first plane may vary along the first curve 116 to maintain the second curve 118 normal to the first curve 116 along the sweep of the first curve 116. According to another embodiment, the second curve 118 may be swept along the first curve 116 with the first curve 116 and the second curve 118 in orthogonal planes. For example, the first curve 116 may be provided in a first plane, e.g., a plane defined by the Y and Z axis and the second curve may be provided in an orthogonal plane, e.g., a plane defined by the X and Z axis. As shown in FIGS. 3 and 4, an embodiment of an implant provided consistent with the preceding design methodology may be generally symmetrical in each of the planes including the first curve string and the second curve string.

In another embodiment the load bearing surface 108 may have a contour and/or geometry resulting from a faired transition between the first curve string 116 and the second curve string 118. That is, the contour and/or geometry of the load bearing surface 108 may be provided by a smooth transition between the first curve string 116 and the second curve string 118 at each quadrant between the first curve string 116 and the second curve string 118. In similar embodiments, providing a faired transition between the first curve string and the second curve string may be achieved using various averaging techniques known for surface generation. Various such averaging techniques are commonly employed in commercial surfacing design and solid modeling computer assisted drafting software packages.

The implant 102 may include a relieved edge 120 around the perimeter of the load bearing surface 108. The relieved edge 120 may include a rounded over, e.g., radiused, edge, a chamfer edge, etc. According to one aspect, when the implant 102 is installed in an articular surface and replacing at least a portion of the articular surface, the relieved edge 120 around the load bearing surface 108 may reduce the presence of a hard edge at a transition between the implant and surrounding articular surface. A reduction and/or elimination of a hard edge at the transition between the load bearing surface of the implant and the surrounding articular surface may reduce and/or eliminate scraping of an interacting articular surface during articulation of the joint. Additionally, the relieved edge 120 may accommodate manufacturing and/or installation tolerances. The relieved edge 120 may permit smooth operation of the joint in a situation in which the implant 102 sits slightly proud above and/or slightly recessed below the surrounding articular surface.

Figure 5:
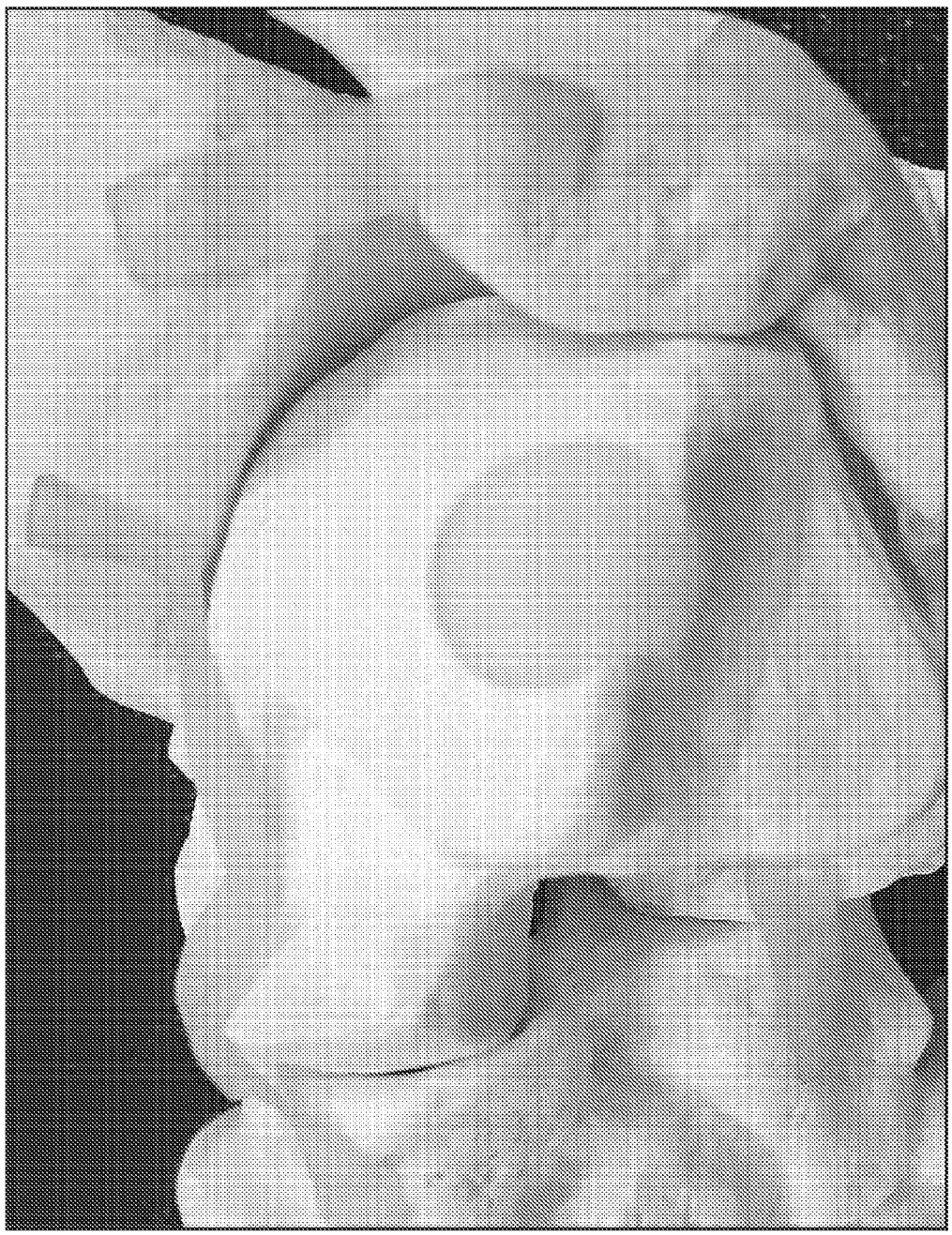
FIG. 5 shows an ankle including a talus implant consistent with the present disclosure.
Figure 6:
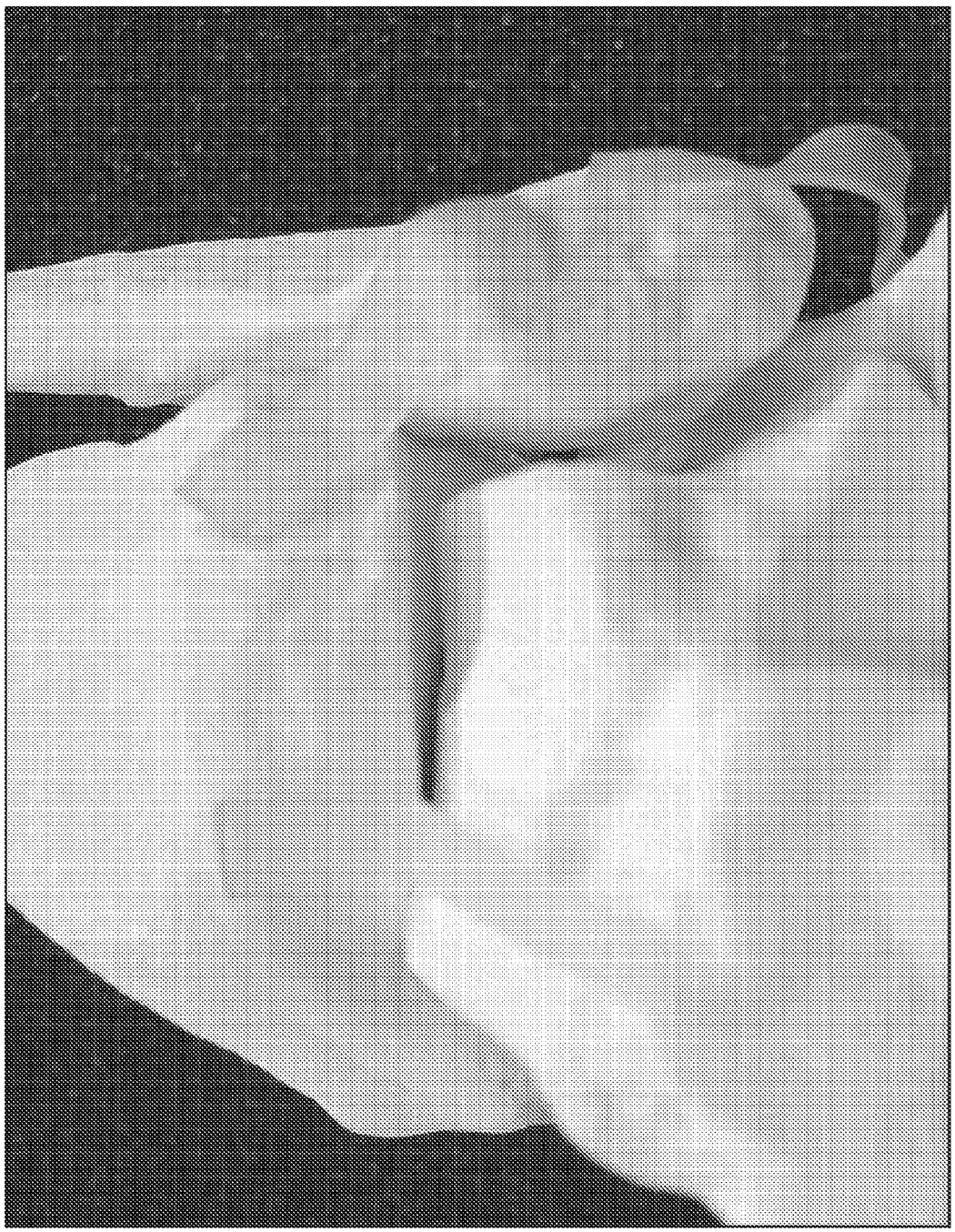
FIG. 6 shows an ankle including a talus implant consistent with the present disclosure.
Figure 7:
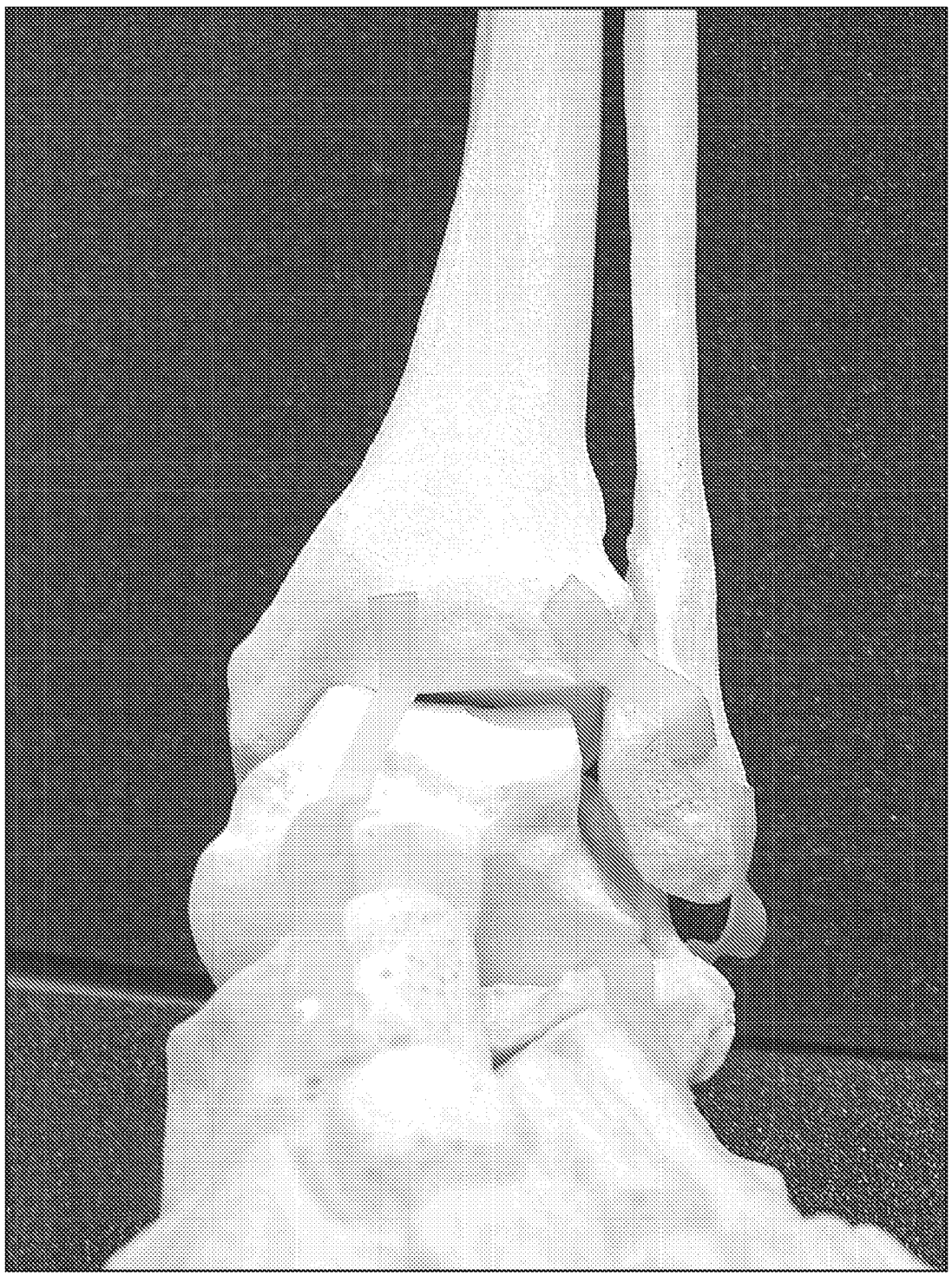
FIG. 7 shows an ankle including a talus implant consistent with the present disclosure.

With particular reference to FIGS. 5 through 7, the load bearing surface 108 of the implant is depicted. As mentioned previously the illustrated implant system 100 may replace a portion of the lateral trochlear ridge of the talus. In one embodiment, an implant site may be prepared using a rotating excision tool, e.g., an excision blade rotating about an axis. Accordingly, the implant site may include a circular excision projected along the axis of rotation of the excision blade. In such an embodiment, the cross-sectional geometry of the implant may generally correspond to the intersection of a projected circular excision with the articular surface of the talus. Various additional and/or alternative excision site preparation tools and techniques are also be contemplated by the present disclosure, along with the attendant changes to the implant configuration.

The location of the fixation element and the orientation of the load bearing surface to the fixation element may be selected to provide secure and stable anchoring of the implant relative to the articular surface. In an embodiment, the implant system may have a configuration wherein the fixation element may extend into the talus at an angle to, and/or spaced from, the lateral ridge. Such a configuration may provide secure anchoring of the implant and/or may reduce the occurrence of tear-out and/or crumbling of the talus resulting from weakening of the talus caused by extension of the fixation element along the lateral face adjacent the trochlear surface. Various additional and/or alternative configurations may also be employed.

Figure 8:
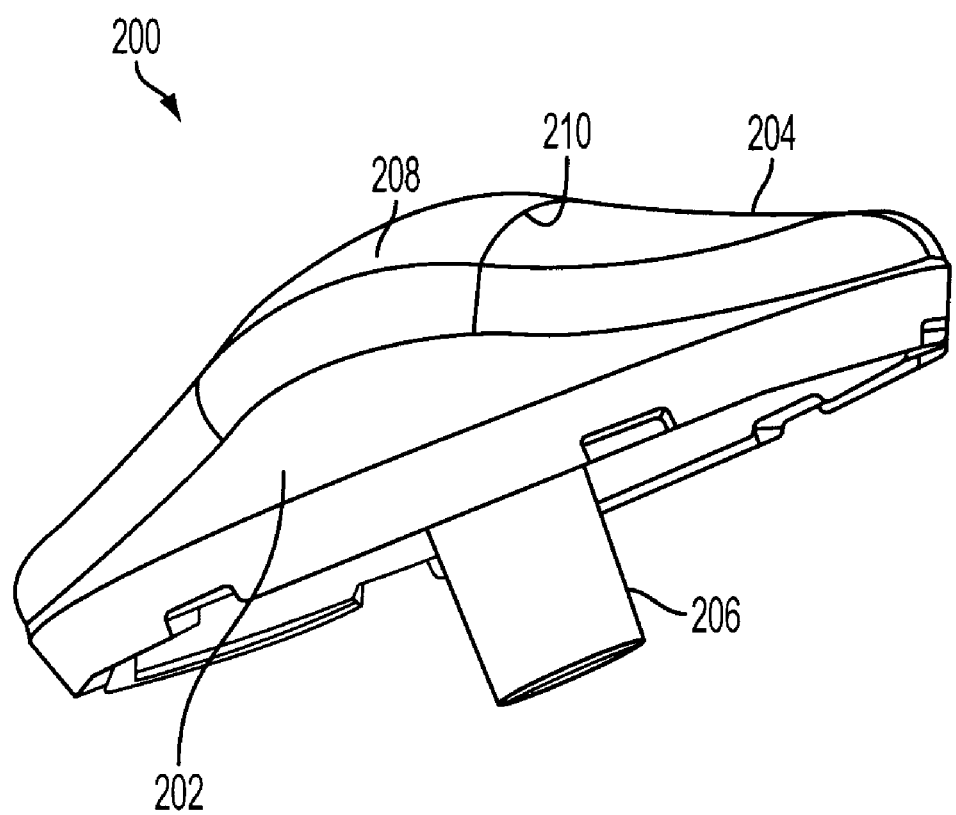
FIG. 8 is a perspective view of another implant consistent with the present disclosure.
Figure 9:
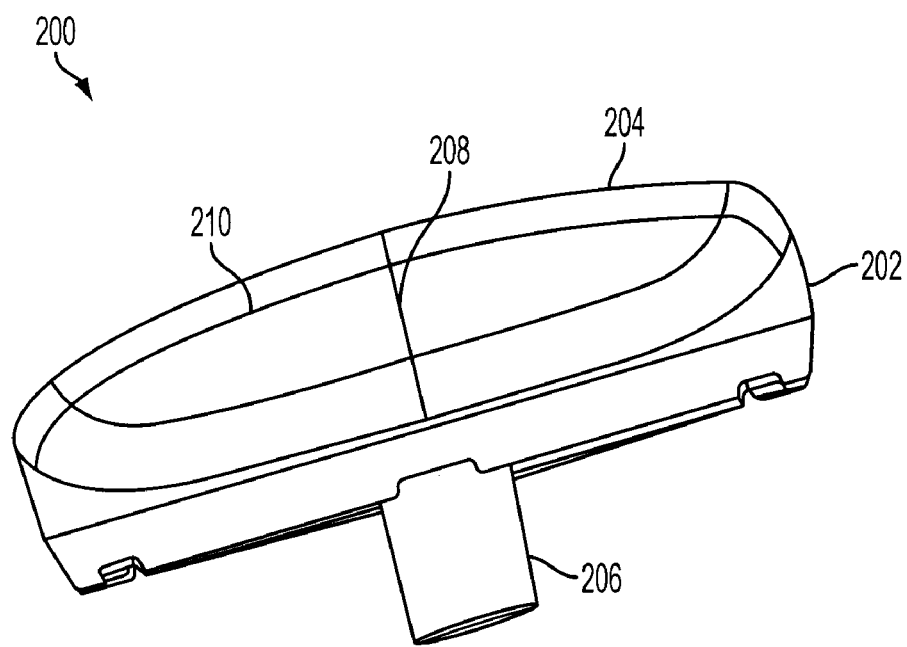
FIG. 9 shows the implant of FIG. 8 from another perspective.

Turning to FIGS. 8 and 9, another embodiment of an implant 200 is shown. The illustrated implant 200 is generally configured to replace at least a portion of an articular surface of a patella. Similar to the previously described embodiment, the implant 200 may generally include an implant body 202 having a load bearing surface 204. The load bearing surface 204 of the illustrated implant 200 may have a contour and/or geometry that may suitably replace at least a portion of an articular surface of a patella. The implant 200 may also include a post 206 capable of coupling with a fixation element (not shown) for anchoring the implant 200 to an articular surface and/or underlying bone. Various other features in addition to, or as an alternative to, a post may be employed for coupling the implant 200 to a fixation element. Furthermore, an embodiment of an implant herein may be provided including an integral fixation element. In such an embodiment, the feature for coupling to a fixation element may optionally be excluded.

Similar to the preceding embodiment, the load bearing surface 204 of the implant 200 may be defined by a first curve string 208 and a second curve string 210. The contour and/or geometry of the load bearing surface 204 may be provided as the first curve string 208 lofted over the second curve string 210, and/or vice-versa. As previously described, the lofted load bearing surface 204 may be achieved by sweeping the first curve string 208 along the second curve string 210. In another embodiment, the load bearing surface of the implant may be provided using averaging algorithms to provide a faired surface in between the first curve string and the second curve string.

Figure 10:
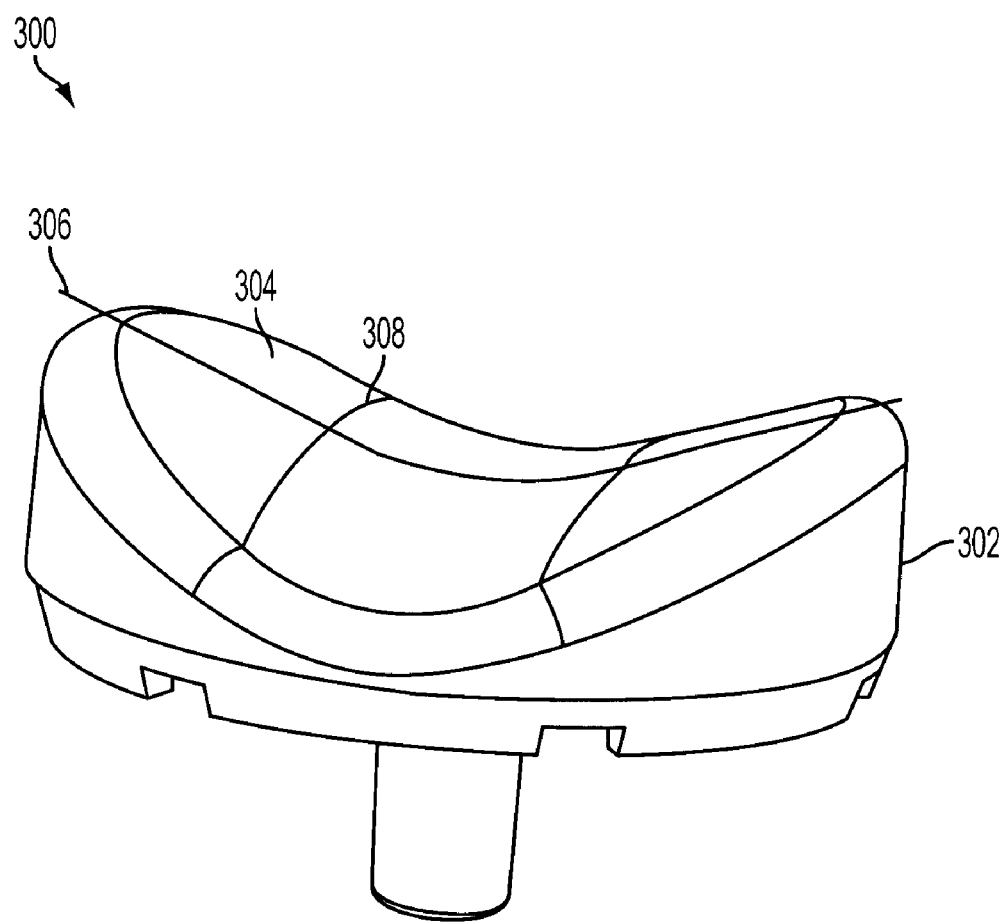
FIG. 10 is a perspective view of yet another implant consistent with the present disclosure.
Figure 11:
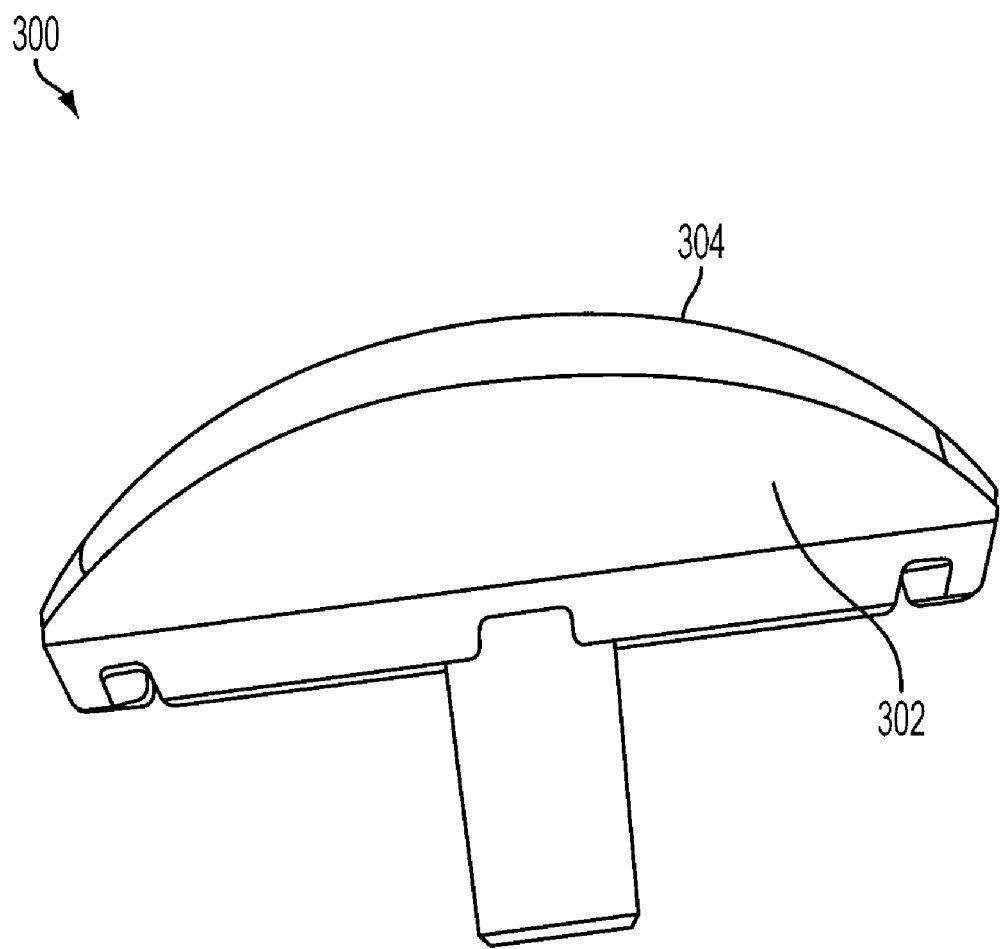
FIG. 11 shows the implant of FIG. 10 from another perspective.

Yet another embodiment of an implant 300 is depicted with reference to FIGS. 10 and 11. The illustrated implant 300 may be capable of replacing at least a portion of a trochlear articular surface, for example a trochlear articular surface of a humerus, etc. As with the previously described embodiments, the implant 300 may generally include an implant body 302 having a load bearing surface 304. The load bearing surface 304 may be defined by a first curve string 306 and a second curve string 308. The load bearing surface 304 may be provided by sweeping the second curve string 308 along the first curve string 306 consistent with the previously described design methodology. Furthermore, the load bearing surface may also be provided as a faired surface defined by a first and second intersecting curve string.

Figure 12:
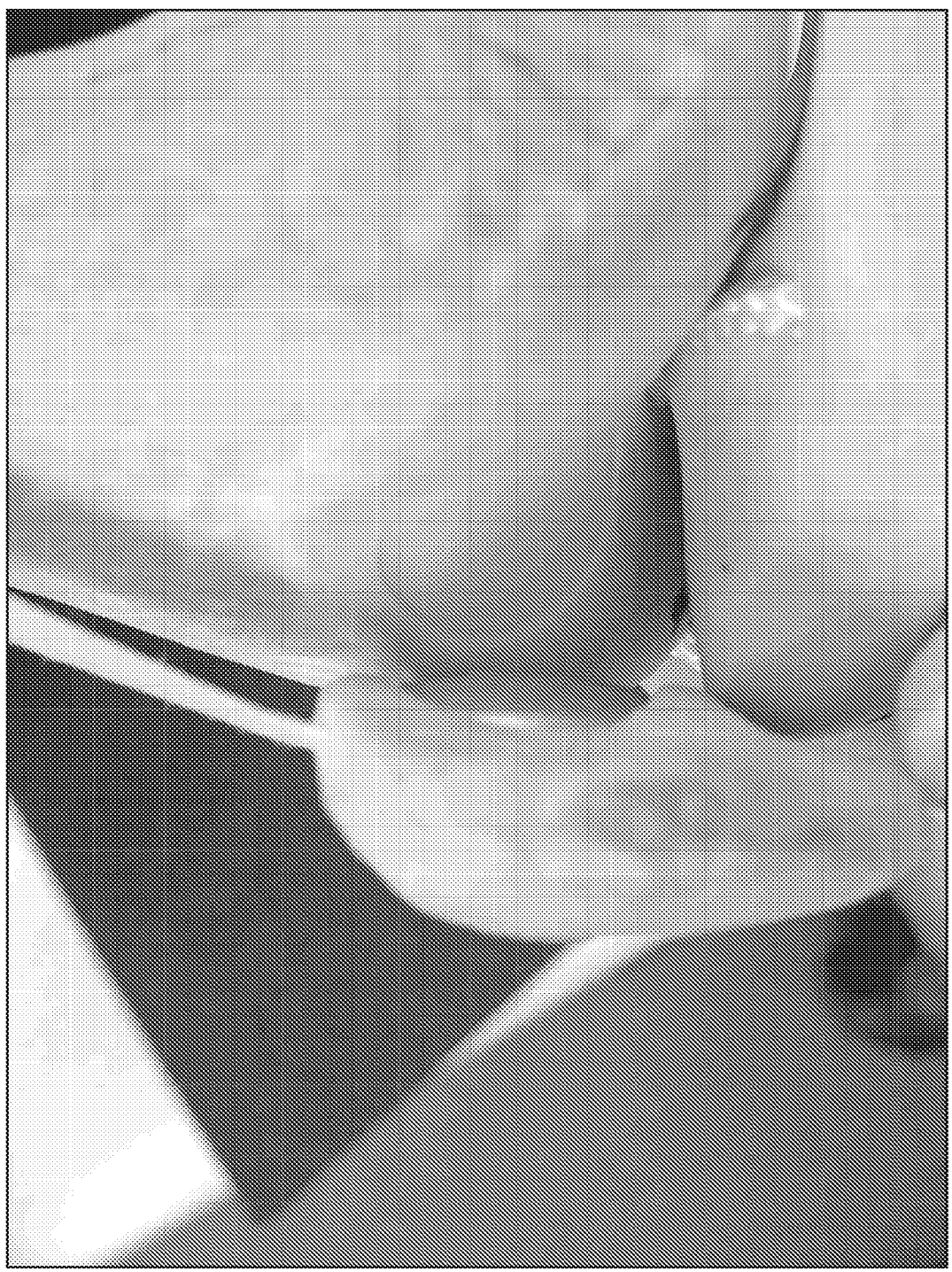
FIG. 12 shows of a trochlear implant consistent with the present disclosure.

Referring to FIG. 12, a model articular surface is shown including an implant capable of replacing at least a portion of a trochlear surface is shown. The implant depicted in FIG. 12 may be generally consistent with the embodiment described with reference to FIGS. 10 and 11. The load bearing surface of the implant, visible in the photograph of the model, may generally have a contour and/or geometry that may generally correspond to the portion of the articular surface being replaced by the implant. In such an embodiment, the implant may provide smooth interaction with a cooperating articular surface, such as depicted in FIG. 12. As previously described, in one embodiment an implant site may be created in an articular surface using a rotating excision tool. A rotating excision tool may provide a circular cutting path that may be projected into the articular surface and/or the underlying subchondral bone. The shape of the implant may, in such an embodiment, generally correspond to the intersection of the circular cutting path and the articular surface.

In summary, according to one aspect, an implant may be provided for replacing a portion of an articular surface. The implant may include a load bearing surface having a contour defined by a first curve string based on a contour of the articular surface in a first plane and by a second curve string based on a contour of the articular surface in a second plane. The first and second planes may be planes which intersect one another. The implant may further include a bone contacting surface.

According to another aspect, the present disclosure may provide an implant system for replacing a portion of an articular surface. The implant system may include an implant having a load bearing surface which is defined by a first and a second curve string. The first curve string may be based on a contour of the articular surface in a first plane and the second curve string may be based on a contour of the articular surface in a second plane. The first and second planes may intersect one another. The implant system may also include a fixation element capable of engaging bone and capable of being coupled to the implant.

According to yet another aspect, the present disclosure may provide a method of forming an implant. The method may include measuring a contour of an articular surface in a first plane and measuring a contour of the articular surface in a second plane, in which the first and second planes are intersecting planes. The method may further include providing an implant body having a load bearing surface. The load bearing surface of the implant body may have a contour defined by the contour of the articular surface in the first plane and the contour of the articular surface in the second plane.

While the embodiments of the implant system illustrated and described above are provided in the context of an implant configured to replace at least a portion of the talus, patella, and humerus trochlea, an implant consistent with the present disclosure may be sized and shaped for replacing at least a portion of various other articular surfaces of the body. Accordingly, consistent with the present disclosure, an implant system may be provided to replace at least a portion of various articular surfaces in addition to a portion of an articular surface of a talus. For example, an implant herein may suitably be employed to replace a portion of an articular surface of a knee joint, a hip joint, a shoulder joint, etc. Accordingly, the foregoing example should not be construed as limiting on the application of an implant consistent with the present disclosure.

What is claimed is:

1. An implant for replacing a portion of an articular surface comprising:
   a load bearing surface having a contour defined by a first curve string based on a contour of said articular surface in a first plane and a second curve string based on a contour of said articular surface in at least a second plane, wherein said second curve string is swept along said first curve string while maintaining said second curve string normal to said first curve string; and
   a bone contacting surface;
   wherein said first curve string is based on a plurality of measurements of the articular surface in the first plane and wherein said second curve string is based on a plurality of measurements of the articular surface in the second plane.

2. An implant according to claim 1, wherein said first and second planes are orthogonal.

3. An implant according to claim 1, further comprising an attachment feature capable of coupling to one of a fixation element or an implant site.

4. An implant according to claim 3, wherein said attachment feature comprises a tapered post capable of engaging a fixation element.

5. An implant according to claim 1, wherein said load bearing surface is relieved around at least a portion of a perimeter of said load bearing surface.

6. An implant system for replacing a portion of an articular surface comprising;
   an implant having a load bearing surface defined by a first curve string based on a contour of said articular surface in a first plane and a second curve string based on a contour of said articular surface in a second plane, said first and second planes intersecting, wherein said second curve string is swept along said first curve string while maintaining said second curve string normal to said first curve string; and
   a fixation element capable of engaging bone and capable of being coupled to said implant;
   wherein said first curve string is based on a plurality of measurements of the articular surface in the first plane and wherein said second curve string is based on a plurality of measurements of the articular surface in the second plane.

7. A system according to claim 6, wherein said first and second planes are orthogonal.

8. A system according to claim 6, wherein said fixation element comprises a threaded region capable of engaging bone.

9. A system according to claim 6, wherein said fixation element comprises an opening and said implant comprises a protrusion capable of being at least partially received in said opening for coupling said implant and said fixation element.

10. A method of forming an implant comprising:
    measuring a contour of an articular surface in a first plane based on a plurality of measurements of the articular surface in the first plane;
    measuring a contour of said articular surface in a second plane based on a plurality of measurements of the articular surface in the second plane, and
    providing an implant body having a load bearing surface, said load bearing surface having a contour defined by said contour of said articular surface in said second plane swept along said contour of said articular surface in said first plane while maintaining said second plane normal to said first plane.

11. A method according to claim 10, wherein said first and second planes are orthogonal.

12. A method according to claim 10, said implant body further comprising a bone contacting surface.

13. A method according to claim 10, wherein measuring said contour of said articular surface in one of said first plane and said second plane comprises one of direct contact contour mapping and radiographic imaging.

* * * * *